United States Patent [19]
Moss

[11] Patent Number: 5,470,337
[45] Date of Patent: Nov. 28, 1995

[54] SURGICAL FASTENER

[76] Inventor: Gerald Moss, RD #1, West Sand Lake, N.Y. 12196

[21] Appl. No.: 291,186

[22] Filed: Aug. 16, 1994

Related U.S. Application Data

[63] Continuation-in-part of Ser. No. 243,946, May 17, 1994.

[51] Int. Cl.⁶ ................................................. A61B 17/04
[52] U.S. Cl. ........................... 606/139; 606/187; 606/232
[58] Field of Search ........................... 606/139, 144–148, 606/232

[56] References Cited

U.S. PATENT DOCUMENTS

| | | |
|---|---|---|
| 3,103,666 | 9/1963 | Bone . |
| 3,675,639 | 7/1972 | Cimber . |
| 3,875,648 | 4/1975 | Bone . |
| 3,910,281 | 10/1975 | Kletschka et al. . |
| 3,961,632 | 6/1976 | Moossum . |
| 4,006,747 | 2/1977 | Kronenthal et al. . |
| 4,126,124 | 11/1978 | Miller . |
| 4,144,876 | 3/1979 | DeLeo . |
| 4,235,238 | 11/1980 | Ogiu et al. ........................... 606/232 |
| 4,669,473 | 6/1987 | Richards et al. ..................... 606/232 |
| 4,705,040 | 11/1987 | Mueller et al. ......................... 604/51 |
| 5,053,046 | 10/1991 | Janese ................................ 606/215 |
| 5,085,661 | 2/1992 | Moss . |

Primary Examiner—Gary Jackson
Attorney, Agent, or Firm—Schmeiser, Olsen & Watts

[57] ABSTRACT

A surgical fastener for securing a hollow organ to an outer tissue layer. The surgical fastener includes first and second opposing fastener heads, a filament portion extending between the first and second fastener heads, and a tubular sleeve which is slidably displaceable along the filament portion. Upon implantation of the surgical fastener, the tubular sleeve is displaced and affixed to the patient to apply substantially equal tension of the implanted heads of the surgical fastener.

10 Claims, 3 Drawing Sheets

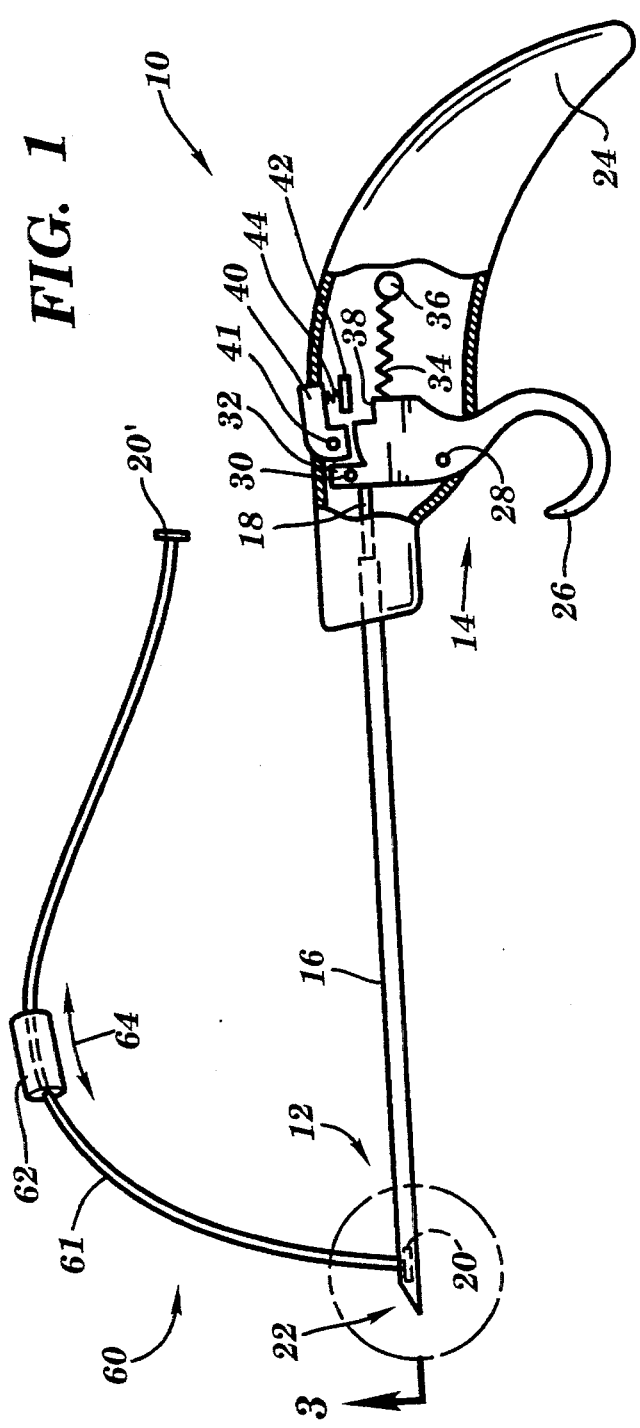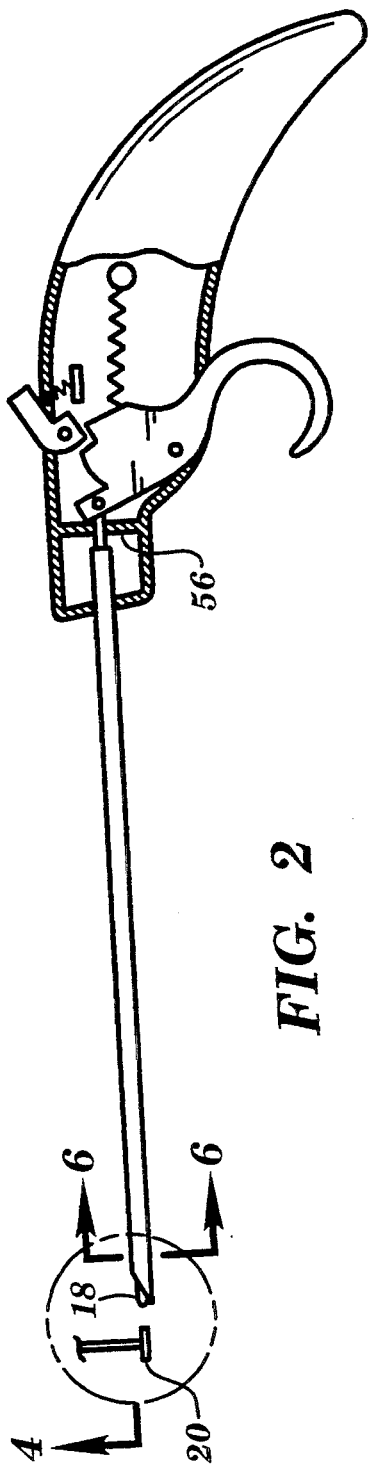

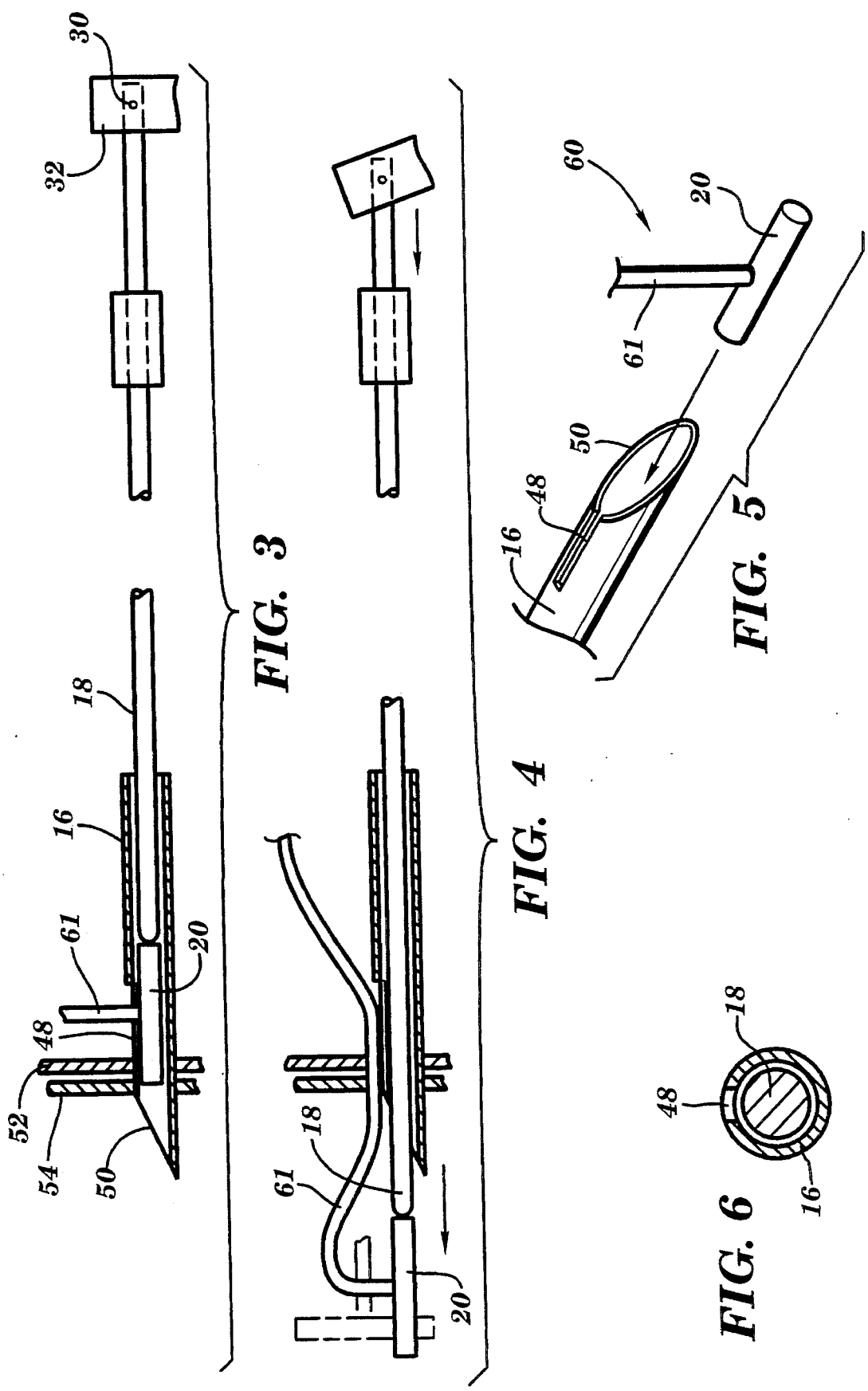

5,470,337

SURGICAL FASTENER

This is a continuation in part of my U.S. patent application Ser. No. 08/243,946, filed on May 17, 1994, entitled SURGICAL FASTENER IMPLANTATION DEVICE.

FIELD OF THE INVENTION

The present invention relates to surgical fasteners and, more particularly, to an "H"-shaped surgical fastener for securing a hollow organ, such as the stomach, to an outer tissue layer. The "H"-shaped fastener includes first and second opposing fastener heads, a filament portion extending between the first and second fastener heads, and a tubular sleeve which is slidably displaceable along the filament portion. In operation, and upon implantation of the "H"-shaped surgical fastener, the tubular sleeve is taped or otherwise affixed to the patient, thereby applying substantially equal tension on the implanted first and second fastener heads.

BACKGROUND OF THE INVENTION

As known in the art, surgical fastener devices have long been employed in a wide variety of medical procedures. Simple filament sutures (stitches), for example, are perhaps the most common type of anchoring device utilized to hold one segment of tissue to another. Recently, to avoid the time required to sew up a wound and tie the sutures, rapid fastening procedures have been developed, wherein an "H" or "T"-shaped fastener is inserted into the tissue about the wound in lieu of a sewn stitch to hold the tissue segments together.

In 1977, Kronenthal et al. received a patent (U.S. Pat. No. 4,006,747) on a surgical fastening method which involves the partial insertion of "H"-shaped fasteners through the tissue adjacent an incision using a hollow needle and a push-rod. Once in place, an end of the fastener is located on each side of the incision, with a connecting filament spanning the incision between the two ends of the fastener. The fastener maintains the tissue in place, thereby facilitating the natural healing process.

The "H"-shaped fastener is also utilized in a number of non-medically related fastening systems. This type of fastener is commonly used in stores to affix price tickets to clothing. A number of devices have been employed to install the fasteners in clothing. Two patents, U.S. Pat. Nos. 3,103,666 and 3,910,281, have been issued to A. R. Bone for hand held devices that aid in the insertion of this type of fastener into clothing.

In recent years, a modification of the fastening system has become prevalent in surgical procedures. Ogiu et al. (U.S. Pat. No. 4,235,238), teaches a system wherein a needle for inserting a "T" shaped fastener is located within the end of an endoscope. Ogiu makes use of a hollow needle that has a longitudinally extending cavity sized to receive the head of the fastener. Once the needle has passed through the tissue on both sides of the wound, an obturator is pushed through the interior of the needle to dislodge the head of the fastener. The needle is then removed and an outer filament end of the fastener is tied to a lock member to maintain the closure of the wound.

Richards et al. (U.S. Pat. No. 4,669,474) illustrates a similar system that makes use of a "T" shaped fastener. Richards implants the head of the fastener into the tissue of a patient using a hollow needle and push-rod (obturator). The head of the fastener is shaped so that it strongly anchors itself to the tissue, therefore providing a secure fastening point within the body. The filament end of the fastener is then externally secured to the skin using a shaped retainer.

Mueller et al. (U.S. Pat. No. 4,705,040) teaches a system that uses a "T" shaped fastener to anchor a hollow organ to the skin. In Mueller, a hollow needle and obturator are again used to implant the head of the fastener. However, Mueller places the head of the fastener within the interior cavity of the organ to be anchored. Mueller then utilizes a movable lock member to secure the outer filament end of the fastener to the exterior of the skin.

The above prior art summaries are merely representative of portions of the inventions disclosed in each reference. In no instance should these summaries substitute for a thorough reading of each individual reference.

Presently available systems and methods for inserting and placing "T"-shaped or "H"-shaped fasteners suffer from a number of serious deficiencies. Firstly, as the inner obturator is pushed in a forward direction through the hollow outer needle to eject the fastener, the operator must push on the obturator along its longitudinal axis while simultaneously attempting to hold the needle stationary. Since the direction of this forwardly directed force is also along the longitudinal axis of the hollow outer needle, and the inner obturator is operationally coupled within the needle, it is extremely difficult to eject the fastener without displacing the outer hollow needle beyond its desired operational orientation. In a medical application, any unnecessary forward displacement of the outer hollow needle may produce unwanted, deleterious tissue damage, potentially increasing the duration of the healing process and/or increasing the risk of postoperative infection. Secondly, since it is generally easy to overcompensate for this forward force, an operator may accidentally pull the needle slightly outwards during the fastener ejection process, possibly resulting in the improper positioning of the fastener within the patient. Thirdly, the outer needle generally incorporates a stop mechanism for limiting the forward displacement of the enclosed obturator. If any difficulties occur during the insertion process, or if the fastener insertion system is inadvertently damaged before, during or after bodily insertion, the stop mechanism could, perhaps, be rendered inoperable or ineffective, thereby permitting the obturator to travel beyond the desired insertion location. As such, needless tissue damage may be inflicted by the unconstrained obturator. Unfortunately, such deficiencies combine to reduce the effectiveness and convenience of currently available "H"-shaped or "T"-shaped fasteners.

Moss (U.S. Pat. No. 5,085,661, incorporated herein by reference) discloses a surgical fastener implantation device which reduces or eliminates the above-described deficiencies. Specifically, the surgical fastener implantation device is designed to implant the head portion of a "T" or "H"-shaped fastener within a body. The surgical fastener implantation device employs a solid delivery needle having a rectangularly shaped cavity proximate the pointed thereof sized to receive the cylindrical head of the fastener. Surrounding the major portion of the needle is a movable sleeve that includes a longitudinally extending slot located at its forward end. Located within the grip portion of the device is a mechanism that is used to selectively cause the sleeve to slide longitudinally on the needle. The grip portion includes a trigger shaped actuator and a position lock that can releasable lock the sleeve in its forward position.

Moss further discloses a method for securing the filament portion of an "H"-shaped surgical fastener upon its successful implantation into a hollow organ of a patient. Specifically, once the fastener heads have been inserted, the doctor fixedly attaches a piece of tape directly to the center area of the filament portion of the fastener. The doctor then pulls the center area of the filament laterally until sufficient tension is applied to the fastener heads to anchor the hollow organ to an outer tissue layer. The doctor subsequently applies the tape to the patient's skin to temporarily secure the filament portion of the "H"-shaped surgical fastener. If the tension applied to the fastener heads is later required to be adjusted, the tape is detached from the patient's skin and is moved appropriately.

When utilizing the filament securing method disclosed above, it is oftentimes difficult to equalize the tension being applied on the fastener heads as the filament portion of the "H"-shaped surgical fastener is secured to the patient's skin. Accordingly, the hollow organ may not be completely secured against the outer tissue layer, thus requiring the doctor to remove and reattach (sometimes repeatedly) the piece of tape to the patient's skin to adjust the tension. Unfortunately, the excessive manipulation of the surgical fastener that is commonly required to properly fasten the "H"-shaped surgical fastener and secure the hollow organ may result in tissue damage proximate the inserted fastener heads. Further, excessive manipulation of the surgical fastener may unintentionally dislodge one or both of the fastener heads, thereby requiring the implantation of an additional surgical fastener.

SUMMARY OF THE INVENTION

In order to avoid the disadvantages of the prior art, the present invention provides a surgical fastener implantation device for quickly and accurately inserting and releasing either a "T"-shaped or "H"-shaped surgical fastener into a body. The invention generally comprises an immovable, hollow outer needle having a beveled, slotted, distal end section for releasably receiving the head of a "T"-shaped or "H"-shaped surgical fastener, a longitudinally displaceable, inner slide mechanism, enclosed within the hollow outer needle, for engaging and ejecting the head of the fastener from the distal end section of the hollow outer needle after proper insertion within a patient, and a trigger shaped actuator, mounted within an ergonomically designed grip, for selectively displacing the inner slide mechanism within the hollow outer needle. A trigger locking mechanism is provided within the grip portion of the fastening device for releasably locking the inner slide mechanism in its forward, postejection position.

The present invention is ideally suited for use in securing organs in place. In operation, the operator loads the head of the fastener into the slot formed in the distal end section of the hollow outer needle. Preferably, the width of the slot is designed to be narrower than the diameter of the fastener head to prevent the premature dislodgement of the fastener head through the top of the slot. Prior to the insertion of the needle into the body tissue, the operator pulls the loose end of the fastener's filament portion toward the handle portion of the device. Next, the operator inserts the beveled end of the hollow outer needle into the body at a location where the tip of the needle will extend into an organ cavity. Upon proper positioning of the fastener head, the operator pulls the trigger shaped actuator, thereby displacing the slide mechanism toward the distal end of the needle, ultimately engaging and ejecting the fastener head within the organ cavity. To insure the complete ejection of the fastener head from the slotted distal end section of the hollow outer needle by preventing any unwanted reverse displacement of the slide mechanism, the trigger locking mechanism engages and locks the inner slide mechanism in its full ejection position, with the distal end of the slide mechanism disposed proximate the apex of the hollow needle bevel. The operator then removes the needle portion of the device from the body and "reloads" the needle with another fastener (or the opposing head of the same fastener—if "H"-shaped).

Advantageously, unlike the surgical fastener devices of the prior art, the instant invention does not require the application of a forwardly directed, longitudinal force during the ejection of the fastener head. Specifically, the trigger shaped actuator of the present invention must be pulled rearwardly to advance the inner slide mechanism in a forward direction within the hollow outer needle during the ejection process. As such, the surgical fastener implantation device substantially eliminates ancillary tissue damage and the inaccurate placement commonly associated with the operation of prior art fastening devices.

The present invention further provides an improved "H"-shaped surgical fastener for securing a hollow organ to an outer tissue layer. The "H"-shaped fastener includes first and second opposing fastener heads, a filament portion extending between the first and second fastener heads, and a tubular sleeve which is slidably displaceable along the filament portion.

When the fastener heads of the improved "H"-shaped surgical fastener of the present invention have been properly inserted, the doctor attaches a piece of tape directly to the tubular sleeve slidably engaging the filament portion of the fastener. The doctor then slides the tubular sleeve to the center area of the filament portion and pulls the center area laterally until sufficient and substantially equal tension is applied to the fastener heads to anchor the hollow organ to an outer tissue layer; the filament portion slides through the tubular sleeve, resulting in the centrally directed displacement of the sleeve. The doctor subsequently applies the tape attached to the tubular sleeve to the patient's skin to temporarily secure the filament portion of the "H"-shaped surgical fastener.

BRIEF DESCRIPTION OF THE DRAWINGS

These and other features of the present invention will become readily apparent upon reading the following detailed description and upon reference to the drawings in which:

FIG. 1 is a side elevational, partially cut-away view of a surgical fastener implantation device and an improved "H"-shaped surgical fastener in accordance with the present invention, with a first fastener head of the "H"-shaped fastener located within the slotted, distal end section of the hollow outer needle;

FIG. 2 illustrates the surgical fastener implantation device of FIG. 1 as the first fastener head is ejected from the slotted, distal end section of the hollow outer needle by the longitudinally displaceable, inner slide mechanism;

FIG. 3 is an enlarged, cross-sectional view of the beveled, slotted, distal end section of the hollow outer needle, prior to the ejection of the fastener head within a hollow organ;

FIG. 4 is an enlarged, cross-sectional view of the beveled, slotted, distal end section of the hollow outer needle, after the ejection of the fastener head within a hollow organ;

FIG. 5 illustrates the loading of a fastener head within the slotted end section of the hollow outer needle;

FIG. 6 is a cross-sectional view of the surgical fastener implantation device, taken along line 6—6 of FIG. 1;

DETAILED DESCRIPTION OF THE DRAWINGS

Figure 7:
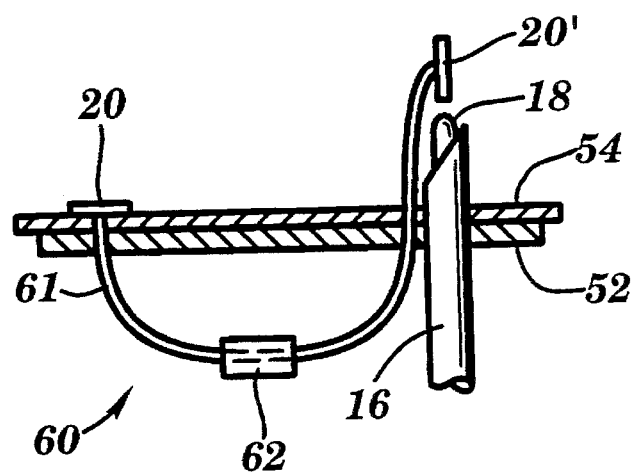
FIG. 7 illustrates the implantation of the first and second heads of the improved "H"-shaped fastener of the instant invention within a hollow organ.

Referring now specifically to the drawings, there is illustrated a surgical fastener implanting device, generally designated as 10, in accordance with a preferred embodiment of the present invention, wherein like reference numerals refer to like components throughout the drawings. Further, an improved "H"-shaped surgical fastener 60, again in accordance with a preferred embodiment of the present invention, is illustrated and described.

The device 10 generally comprises an insertion portion 12 and a grip portion 14. The insertion portion 12 basically includes an immovable, hollow outer needle 16 and an elongated, substantially cylindrical, longitudinally displaceable, inner slide mechanism 18 for selectively engaging and ejecting the head 20 of an "H"-shaped fastener 60 disposed within the beveled, slotted, distal end section 22 of the hollow outer needle 16.

As shown throughout the drawings, the improved "H"-shaped surgical fastener 60 includes first and second opposing fastener heads, 20 and 20', respectively, a filament portion 61 extending between the first and second fastener heads, and a tubular sleeve 62 which is slidably displaceable along the filament portion 61 as depicted by directional arrow 64. As shown, the tubular sleeve 62 preferably has a length substantially smaller than the length of the filament portion 61. The function of the tubular sleeve 62 will be addressed in detail hereinbelow.

The inner slide mechanism 18, when in its retracted position as detailed in FIG. 1, is fully enclosed within the hollow outer needle 16. As illustrated in FIG. 2, upon the rearwardly directed actuation of a manually actuated translation system (described hereinafter), the inner slide mechanism 18 is longitudinally displaced within the hollow outer needle 16, thereby ejecting the head 20 of an "H"-shaped fastener 60 from the beveled, slotted, distal end section 22 of the hollow outer needle 16. The needle is preferably of 18 gauge and has a length of approximately six inches. It should be noted that the surgical fastener implanting device 10 is described in conjunction with an "H"-shaped surgical fastener. However, as should be readily apparent to those having ordinary skill in the art, the implantation device 10 may be utilized to insert other suitably-shaped fasteners into a patient.

The grip portion 14 has a rearwardly extending, ergonomically designed handle portion 24 that is sized to securely and comfortably fit within a user's clenched hand. Housed within the grip portion 24 is a manually actuated translation system that enables the user to selectively displace the inner slide mechanism 18 within the hollow outer needle 16.

The translation system includes a trigger shaped actuator 26 that is pivotally mounted within the grip portion 14 about a pivot pin 28. An end section of the longitudinally displaceable, inner slide mechanism 18 is similarly pivotally mounted about a pivot pin 30 to an upper, anterior portion 32 of the trigger shaped actuator 26. The hollow outer needle 16 is suitably anchored within the forward end of the grip portion 14 in a conventional manner, and is not further detailed.

A spring 34, which is affixed within the grip portion 14 at 36, is attached to a posterior portion of the trigger shaped actuator 26. The spring 34 is utilized to provide a clockwise biasing of the actuator 26. A top surface of the actuator 26 further includes a step 38 that is adapted to engage a lock member 40 in response to a rearwardly displacement of the actuator 26. The lock member 40 pivots about a pivot pin 41 and is coupled to an anchor 42 by a compression spring 44 which is adapted to provide a counterclockwise biasing of the lock member 40.

FIGS. 1, 3 and 5 illustrate the initial loading and positioning of a fastener head 20 of the improved "H"-shaped surgical fastener 60 within the beveled, slotted, distal end section 22 of the hollow outer needle 16. As most clearly shown in FIG. 5, the generally cylindrical head portion 20 (typically 1 cm in length) of the "H"-shaped fastening member 60 is placed within a slot 48 formed rearwardly of the beveled tip 50 of the needle, with the filament portion 61 of the fastener 60 extending upwardly through the slot 48. As detailed in cross-section in FIG. 6, the slot 48 is formed through the top of the hollow outer needle 16. Preferably, the beveled needle tip 50 has a 25 degree bevel, and the slot 48 extends approximately 7 mm from the heel of the bevel. Once the fastener head 20 has been appropriately positioned within the slot 48, the beveled needle tip 50 is inserted into the interior of a hollow organ, such as the stomach, through the outer tissue layer 52 of the patient and the outer surface 54 of the organ.

Referring now specifically to FIGS. 2 and 4, there is illustrated the ejection of a fastener head 20 from the distal end section of the hollow outer needle 16. Specifically, as the trigger shaped actuator 26 is moved rearwardly from the position shown in FIG. 1, thereby pivoting the upper, anterior portion 32 of the actuator 26 in a forward direction about the pivot pin 28, the inner slide mechanism 18 is longitudinally displaced forwardly within the hollow outer needle, ultimately engaging and propelling the fastener head 20 from the end of the outer needle. When the trigger shaped actuator 26 reaches its rearwardmost position, the end of the inner slide mechanism extends to the apex of the beveled needle tip 50. Advantageously, the forward movement of the inner slide mechanism 18 is limited by the internal configuration of the grip portion 14. Specifically, as shown in FIG. 2, the grip portion 14 incorporates a front blocking wall 56 which is adapted to limit the forward rotation of the upper, anterior portion 32 of the actuator 26 about the pivot pin 28. As such, the end of the inner slide mechanism 18 is prevented from extending beyond the apex of the beveled needle tip 50, even if the actuator mechanism is defective or inadvertently damaged. As the trigger shaped actuator 26 reaches its rearwardmost position, the lock member 40 rotates in a counterclockwise direction due to the biasing of spring 44, ultimately engaging the step 38 which is formed proximate the top of the actuator 26. At this point, the inner slide mechanism 18 is locked in its postejection orientation.

The fastener ejection process may be accomplished by any of a number of different methods. The user can pull slightly on the filament portion 61 of the fastener 60 as the inner slide mechanism 18 is displaced forwardly within the needle 16, thereby facilitating the ejection of the fastener head 20 from the slot 48. A second method of release is based on the material used for the fastener 60. Preferably, the fastener 60 is made from a semi-resilient plastic such as nylon or polypropylene. The filament portion 61 is joined to the filament head 20 substantially perpendicular to the longitudinal axis of the fastener head. When the fastener is first inserted into the body, the filament 61 is pulled slightly so that it lies adjacent the body of the needle. As illustrated in FIG. 4, this causes a moment type of force on the end of the fastener due to the approximately ninety degree bending of the filament end adjacent the head portion of the fastener (i.e.—the filament is caused to lie substantially parallel to the longitudinal axis of the fastener head). When the inner slide mechanism 18 is displaced forwardly within the hollow outer needle 16, subsequently engaging the fastener head 20, the fastener head is propelled out of the slot 48 by the inherent resilience of the filament 61. The postejection orientation of the filament head 20, regardless of the ejection process, is illustrated in phantom in FIG. 4. Once the fastener head is ejected, the needle is withdrawn from the patient.

FIG. 7 shows a second end of the improved "H"-shaped fastener 60 of the present invention being inserted into a hollow organ. As shown, a first fastener head 20 has already been properly implanted. After loading the second fastener head 20' into the surgical fastener implantation device 10, and subsequently inserting it into the body near the secured first head portion 20 of the fastener, the second fastener head 20' may be ejected and implanted as described above, thereby completing the attachment of the "H"-shaped fastener 60.

Figure 8:
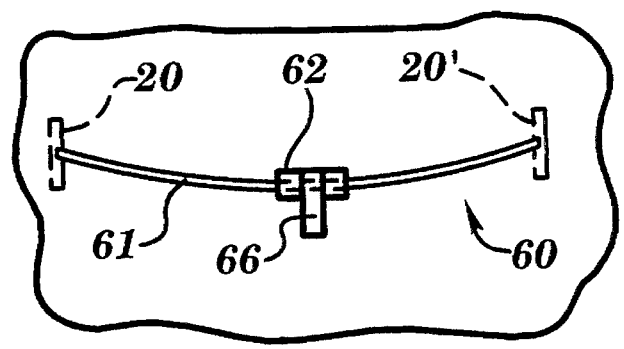
FIG. 8 is a plan view of the body in the region shown in FIG. 7, with the filament portion of the improved "H"-shaped fastener secured to the exterior of a patient's skin.

After the fastener heads 20, 20' of the improved "H"-shaped surgical fastener 60 have been properly implanted, the filament portion 61 is secured to the skin of the patient as illustrated in FIG. 8. FIG. 8 shows an exterior view of the patient's body in the region where the fastener heads 20, 20' have been implanted, with the fastener heads shown in phantom.

Subsequent to the implantation of the "H"-shaped surgical fastener 60, the doctor attaches a piece of tape 66 to the tubular sleeve 62. As detailed above, the tubular sleeve 62 slidably engages the filament portion 61 of the surgical fastener 60 and may be slidably displaced along the filament portion 61. The doctor then slides the tubular sleeve 62 toward the center area of the filament portion 61 and pulls the center area laterally until sufficient and substantially equal tension is applied to the fastener heads 20, 20' to anchor the hollow organ against the outer tissue layer 52 of the patient (see FIG. 7). The doctor subsequently applies the tape 66 attached to the tubular sleeve to the patient's skin to temporarily secure the filament portion 61 of the "H"-shaped surgical fastener. If, for some reason, the tension is later required to be readjusted, the tape 66 is removed from the patient, and the tubular sleeve 62 is slidably displaced to a new location which provides the fastener heads 20, 20' with the proper degree of tension. Upon repositioning, the tape 66 is reattached to the patient.

The foregoing description of the preferred embodiments of the invention has been presented for purposes of illustration and description. It is not intended to be exhaustive or to limit the invention to the precise form disclosed, and obviously many modifications and variations are possible in light of the above teaching. Such modifications and variations that may be apparent to a person skilled in the art are intended to be included within the scope of this invention as defined by the accompanying claims.

I claim:

1. A surgical fastener including:

first and second opposing surgical fastener heads;

a filament portion attached to and extending between said first and second fastener heads;

a sleeve slidably displaceable along said filament portion; and means, operatively attached to said sleeve, for releasably attaching said sleeve in a position such that substantially equal tension may be applied to each said surgical fastener head after insertion of each said surgical fastener head into a patient.

2. The surgical fastener according to claim 1, wherein said surgical fastener is an "H"-shaped surgical fastener.

3. The surgical fastener of claim 1, wherein said means for releasably attaching is tape and said surgical fastener is adapted to secure a hollow organ to an outer tissue layer of a patient.

4. The surgical fastener according to claim 1, wherein said filament portion has a first length, and wherein said tubular sleeve has a length substantially smaller than the length of the filament portion.

5. The surgical fastener of claim 1, wherein said sleeve is tubular.

6. The surgical fastener of claim 5, wherein said filament extends along a longitudinal axis of said tubular sleeve.

7. A surgical insertion apparatus and surgical fastener therefore comprising:

a shaped surgical fastener including first and second opposing head portions, a filament portion attached to and extending between said first and second head portions, and a tubular sleeve slidably displaceable along said filament portion, and a releasably securable attachment device operatively attached to said tubular sleeve, for attaching said tubular sleeve in a position such that substantially equal tension may be applied to each said surgical fastener head after insertion of each said fastener head into a patient;

a needle member having a distal end section for removably accommodating a head portion of said shaped fastener;

an ejection mechanism operatively attached to said needle member, for ejecting said head portion from said needle member; and an actuator, operably coupled to said ejection mechanism, for ejecting the head portion of said shaped fastener from the distal end section of said needle member subsequent to an insertion of the distal end section of said needle member into a hollow organ of said patient, said tubular sleeve remaining outside of said patient after the ejection of said head portion.

8. The surgical fastener insertion apparatus according to claim 7, wherein said actuator includes a trigger, and wherein the head portion of said shaped fastener is ejected upon a displacement of said trigger away from the distal end section of said needle member.

9. The surgical insertion apparatus and surgical fastener of claim 7, wherein said releasably securable attachment device is tape.

10. A method for anchoring a hollow organ comprising the steps of:

A) providing a surgical fastener having first and second opposing fastener heads, a filament portion extending between said first and second fastener heads, and a tubular sleeve slidably displaceable along said filament portion;

B) inserting the first fastener head of said surgical fastener into a hollow organ of a body;

C) inserting the second fastener head of said surgical fastener into said hollow organ, said tubular sleeve remaining exterior to said body;

G) displacing said tubular sleeve to anchor said hollow organ; and

H) removably securing said tubular sleeve to said body.

* * * * *